US010472663B2

(12) United States Patent
Fernández García et al.

(10) Patent No.: US 10,472,663 B2
(45) Date of Patent: Nov. 12, 2019

(54) PROCEDURE FOR THE RAPID DETERMINATION OF BACTERIAL SUSCEPTIBILITY TO ANTIBIOTICS THAT INHIBIT PROTEIN SYNTHESIS

(71) Applicant: ABM TECHNOLOGIES, LLC, Navasota, TX (US)

(72) Inventors: José Luis Fernández García, Oleiros (ES); Jaime Gosálvez Berenguer, Colmenar Viejo (ES); Germán Bou Arévalo, Culleredo (ES); Maria Tamayo Novas, A Coruña (ES); Rebeca Santiso Brandariz, A Coruñ (ES); Fátima María Otero Fariña, Oleiros (ES)

(73) Assignee: ABM Technologies, LLC, Navasota, TX (US)

(*) Notice: Subject to any disclaimer, the term of this patent is extended or adjusted under 35 U.S.C. 154(b) by 0 days.

(21) Appl. No.: 15/000,743

(22) Filed: Jan. 19, 2016

(65) Prior Publication Data
US 2016/0208307 A1    Jul. 21, 2016

(30) Foreign Application Priority Data
Jan. 21, 2015   (EP) .................................... 15382009

(51) Int. Cl.
*C12Q 1/18*       (2006.01)
*C12Q 1/68*       (2018.01)

(52) U.S. Cl.
CPC ............... *C12Q 1/18* (2013.01); *C12Q 1/68* (2013.01)

(58) Field of Classification Search
None
See application file for complete search history.

(56) References Cited

U.S. PATENT DOCUMENTS

| 4,622,297 | A | 11/1986 | Kappner et al. |
| 6,391,577 | B1* | 5/2002 | Mikkelsen ............... C12Q 1/24 435/182 |
| 6,750,038 | B1* | 6/2004 | Nakane .................... C12Q 1/18 435/32 |
| 2007/0178450 | A1 | 8/2007 | Wheeler et al. |
| 2010/0129803 | A1 | 5/2010 | Gosalvez Berenguer et al. |
| 2012/0045820 | A1 | 2/2012 | Stroman |
| 2012/0122831 | A1 | 5/2012 | Sauer-Budge et al. |
| 2013/0008793 | A1 | 1/2013 | Chung et al. |
| 2016/0102334 | A1 | 4/2016 | Jung et al. |

FOREIGN PATENT DOCUMENTS

| CA | 2842865 A1 | 1/2013 |
| EP | 0135023 A2 | 7/1984 |
| WO | 9219763 A1 | 11/1992 |
| WO | 9321511 A1 | 10/1993 |
| WO | WO-9937799 A1 * | 7/1999 ............... C12Q 1/18 |
| WO | 2012021802 A2 | 2/2012 |
| WO | 2013014324 A1 | 3/2013 |
| WO | 2015003047 A1 | 1/2015 |

OTHER PUBLICATIONS

Turnidge et al. (Setting and Revising Antibacterial Susceptibility Breakpoints; Clinical Microbiology Reviews; 20(3):391-408; see p. 391, Introduction).*
Kitano et al. 1979 (Triggering of Autolytic Cell Wall degradation in *Escherichia coli* by Beta-Lactam Antibiotics; Antimicrobial Agents and Chemotherapy16(6): 838-848). (Year: 1979).*
Tamayo et al. 2013 (Rapid Determination of Colistin Resistance in Clinical Strains of Acinetobacter baumannii by Use of the Micromax Assay; Journal of Clinical Microbiology 51(11):3675-3682). (Year: 2013).*
Peterson et al. 2008, Review Article: Antibiotic policy and prescribing strategies for therapy of extended-spectrum b-lactamase-producing Enterobacteriaceae: the role or piperacillin-tazobactam; Clin Microbiol Infect 14 (Suppl 1): 181-184). (Year: 2008).*
Leekha et al. 2011 General Principles of Antimicrobial Therapy; Symposium on Antimicrobial Therapy; Mayo Clin Proc. 2011;86(2):156-167) (Year: 2011).*
EPO Extended Search Report dated Jul. 13, 2015 issued in related EP No. 15382009.7.
International Search Report dated May 9, 2016 issued in related PCT No. PCT/US2016/013835.
Santiso, R. et al. "A Rapid In Situ Procedure for Determination of Bacterial Susceptibility or Resistance to Antibiotics That Inhibit Peptidoglycan Biosynthesis." BMC Microbiology, vol. 11, No. 1, 2011, p. 191.
Buyck, J. M. et al. "Increased Susceptibility of Pseudomonas Aeruginosa to Macrolides and Ketolides in Eukaryotic Cell Culture Media and Biological Fluids Due to Decreased Expression of oprM and Increased Outer-Membrane Permeability." Clinical Infectious Diseases. vol. 55, No. 4, 2012, pp. 534-542.
Tamayo, M. et al. "Rapid Determination of 3-5 Colistin Resistance in Clinical Strains of Acinetobacter baumannii by Use of the Micromax Assay." Journal of Clinical Microbiology. vol. 51, No. 11, 2013, pp. 3675-3682.

(Continued)

*Primary Examiner* — Mary Maille Lyons
(74) *Attorney, Agent, or Firm* — Ryan Christensen; Hashim Rahman

(57) ABSTRACT

The present invention relates to a method for the rapid evaluation of bacterial susceptibility or non-susceptibility of bacteria to antibiotics that inhibit protein synthesis. The rationale is to identify bacterial responses that depend or are influenced by protein synthesis. If this response is prevented or reduced by the antibiotic that inhibits the protein synthesis, the bacteria are susceptible to this antibiotic. Otherwise, if the response keeps similar despite the incubation with the antibiotic, the bacteria are not susceptible or resistant to this antibiotic. These responses could be determined at the DNA lev-el, cell wall level, morphological level or any other experimental approach, including metabolic, bio-chemical, physiological or genetic processes.

7 Claims, 6 Drawing Sheets

(56) References Cited

OTHER PUBLICATIONS

Tamayo, M. et al. "Rapid Assessment of the 3-5 Effect of Ciprofloxacin on Chromosomal DNA From *Escherichia coli* Using an In Situ DNA Fragmentation Assay." BMC Microbiology., vol. 9, No. 1, 2009, p. 69.
Tamayo, M. et al. "Cell Wall Active Antibiotics Reduce Chromosomal DNA Fragmentation by Peptidoglycan Hydrolysis in *Staphylococcus aureus*." Archives of Microbiology. vol. 194, No. 12, 2012, pp. 967-975.
Bou, G. et al. "Fast Assessment of Resistance to Carbapenems and Ciprofloxacin of Clinical Strains of Acinetobacter baumannii." Journal of Clinical Microbiology. vol. 50, No. 11, 2012, pp. 3609-3613.
Santiso, R. et al. "Rapid and Simple Determination of Ciprofloxacin Resistance in Clinical Strains of *Escherichia coli*." Journal of Clinical Microbiology. vol. 47, No. 8, 2009, pp. 2593-2595.
Mellroth. P. et al. "LytA, Major Autolysin of *Streptococcus pneumoniae*, Requires Access to Nascent Peptidoglycan." The Journal of Biological Chemistry vol. 287, No. 14, pp. 11018-11029, Mar. 30, 2012.
Jorgensen, J. H. "Antimicrobial Susceptibility Testing: A Review of General Principles and Contemporary Practices." Clinical Infectious Diseases 2009; 49: 1749-55.
Kitano, K. "Triggering of Autolytic Cell Wall Degradation in *Escherichia coli* by Beta-Lactam Antibiotics." Antimicrobial Agents and Chemotherapy, vol. 16, No. 6, Dec. 1979, p. 838-848.
Lambert, T. "Antibiotics That Affect the Ribosome." Rev. sci. tech. Off. int. Epiz., 2012, 31 (1), 57-64.
Rolain, J. M. et al. "Real-time PCR for Universal Antibiotic Susceptibility Testing." Journal of Antimicrobial Chemotherapy (2004) 54, 538-541.
Van Belkum, A. et al. "Biomedical Mass Spectrometry in Today's and Tomorrow's Clinical Microbiology Laboratories." Journal of Clinical Microbiology, 2012. p. 1513-1517.
Van Belkum, A. et al. "Next-Generation Antimicrobial Susceptibility Testing." Journal of Clinical Microbiology, vol. 51 No. 7, 2013. p. 2018-2024.
Baldoni, D. "Performance of Microcalorimetry for Early Detection of Methicillin Resistance in Clinical Isolates of *Staphylococcus aureus*." Journal of Clinical Microbiology. vol. 47, No. 3, Mar. 2009, p. 774-776.
Baraban, L. "Millifluidic Droplet Analyser for Microbiology." Lab Chip, 2011, 11, 4057-4062.
Bauer, A. W. et al. "Antibiotic Susceptibility Testing by a Standard Single Disk Method." The American Journal of Clinical Pathology. vol. 20, No. 3, 1966.
Godin, M. "Using Buoyant Mass to Measure the Growth of Single Cells." Nat Methods. May 2010 ; 7(5): 387-390.
Hoettges, K. "Rapid determination of antibiotic resistance in *E. coli* using dielectrophoresis" Phys. Med. Biol. 52 (2007) 6001-6009.
Kinnunen, Paivo, et al. "Self-Assembled Magnetic Bead Biosensor for Measuring Bacterial Growth and Antimicrobial Susceptibility Testing." mall. Aug. 20, 2012; 8(16): 2477-2482.
Chantratita, N. C. et al. "Antimicrobial resistance to ceftazidime involving loss of penicillin-binding protein 3 in Burkholderia pseudomallei." PNAS, vol. 108, No. 41, 2011.
Ingham, Colin J. et al. "Rapid Antibiotic Sensitivity Testing and Trimethoprim-Mediated Filamentation of Clinical Isolates of the Enterobacteriaceae Assayed on a Novel Porous Culture Support." Journal of Medical Microbiology (2006), 55, 1511-1519.
Limbert, M. et al. "Cefodizime, an Aminothiazolylcephalosporin I. in Vitro Activity." The Journal of Antibiotics. vol. XXXVII, No. 8. 1984.
Braga, Pier et al. "Cefodizime: Effects of Sub-Inhibitory Concentrations on Adhesiveness and Bacterial Morphology of *Staphylococcus aureus* and *Escherichia coli*: Comparison With Cefotaxime and Ceftriaxone." Journal of Antimicrobial Chemotherapy (1997) 39, 79-84.
Curtis, N.A., et al., "Competition of beta-lactam antibiotics for the penicillin-binding proteins of Pseudomonas aeruginosa, Enterobacter cloacae, Klebsiella aerogenes, Proteus rettgeri and *Escherichia coil*: comparison with antibacterial activity and effects upon bacterial morphology", Antimicrobial Agents and Chemotherapy 16, No. 3 (1979): 325-328.
Nakao, M., et al., "Light and Electron Microscopy of the Morphological Response of *Escherichia coli* and Serratia Marcescens to Cefmenoxime (CE-1365), A new Broad-Spectrum Cephalosporin", Journal of Antibbiotics, 34.8 (1981): 1046-1054.
Wiegand, I., et al., "Effect of inoculum density on susceptibility of Plesiomonas shigelloides to cephalosporins", Journal of Antimicrobial Chemotherapy 54, No. 2 (2004): 418-423.
Nathan, P., et al., "Identification of two new cell division genes that affect a high-molecular-weight penicillin-binding protein in Caulobacter crescentus", Journal of Bacteriology 170, No. 5 (1988): 2319-2327.
Sass, P., et al., "Antibiotic acyldepsipeptides activate ClpP peptidase to degrade the cell division protein Ftsz", Proceedings of the National Academy of Sciences 108, No. 42 (2011): 17474-17479.
Hashimoto, H., et al., "Rapid Bacterial Testing Method by Size Distribution Measurement with Laser Light Scattering", IEICE Transactions (1976-1990) 68, No. 5 (1985): 304-308.
Hashimoto, H., et al., "Database Compendex: Measurement of Bacterial Size Distribuion Using Laser Light Scattering" On-line, Engineering Information, Inc., NY, (1984) 1 pp.
Turnidge et al. "Setting and Revising Antibacterial Susceptibility Breakpoints." Clinical Microbiology Reviews, vol. 20, No. 3, pp. 391-408. Jul. 2007.
Lorian, V. et al., "Weight and morphology of bacteria exposed to antibiotics" The Influence of Antibiotics on the Host-Parasite Relationship II, 1985. pp. 65-66.
Lorian, Victor et al., "Minimal Antibiotic Concentrations of Aminoglycosides and ,B-Lactam Antibiotics for Some Gram-Negative Bacilli and Gram-Positive Cocci" The Journal of Infectious Diseases, vol. 139, No. 5, May 1979. pp. 599-603.
Tanaka, Mayumi et al., "In Vitro and In Vivo Activities of DQ-2556 and Its Mode of Action" Antimicrobial Agents and Chemotherapy, Dec. 1992. pp. 2595-2601.
Decoster, A, "Classification Des Antibiotiques" Antibiotiques, 2012.
Cushnie, Tim et al., "Morphological and ultrastructural changes in bacterial cells as an indicator of antibacterial mechanism of action" Cell. Mol. Life Sci., 2016. pp. 1-28.
Choi, J et al., "Single-Cell Morphological Analysis for Rapid Antimicrobial Susceptibility Test" Transducers, 2015. pp. 730-734.
Otero, Fatima et al., "Rapid Detection of Antibiotic Resistance in Gram-Negative Bacteria Through Assessment of Changes in Cellular Morphology" Microbial drug resistance, vol. 23, No. 2, 2017. pp. 157-162.
Kjeldsen, Thea et al., "Extended spectrum Beta-lactamase-producing *Escherichia coli* forms filaments as an initial response to cefotaxime treatment" BMC Microbiology, 2015. pp. 2-6.
Brody's human pharmacology, "Bacterial Cell Wall Synthesis Inhibitors—Brody's Human Pharmacology: With Student Consult", [cite Jul. 9, 2017] disponible sur :[http://doctorlib.info/pharmacology/pharmacology/48.html].
Fredborg, Marlene et al., "Automated image analysis for quantification of filamentous bacteria" BMC Microbiology, 2015. pp. 1-8.
Zhanel, George et al., "Subinhibitory antimicrobial concentrations review of in vitro and in vivo data" Can J Infect Dis, vol. 3, No. 4, Jul. 1992. pp. 193-201.
Chung, Cheng-Che et al., "Screening of Antibiotic Susceptibility to A-Lactam-Induced Elongation of Gram-Negative Bacteria Based on Dielectrophoresis" Analytical chemistry, vol. 84, Dec. 2012. pp. 3347-3354.
Leboffe, Michael et al., "A photographic atlas for the microbiology laboratory 4th edition" USA: Morton Publishing, 2011.
Van Boven, CPA et al "Size determination by the filtration method of the reproductive elements of group A Streptococcal L Forms" J Gen Microbiol, vol. 52, 1968. pp. 403-412.
Chau, Frangoise et al., "Flow cytometry as a tool to determine the effects of cell wall active antibiotics on vancomycin susceptible and resistant Enterecoccus faecalis strains" Antimicrobial Agents and Chemotherapy, 2011. pp. 395-398.

(56) References Cited

OTHER PUBLICATIONS

Nuding, Sabine et al., "Detection, identification and susceptibility testing of bacteria by flow cytometry" Bacteriology & Parasitology, 2013. pp. 1-9.
Lacoste, Judith, "Transmitted light contrasting techniques : BF,DF,PC, pol,DIC" McGill systems biology program, 2010.

* cited by examiner

FIG. 13    FIG. 14    FIG. 15
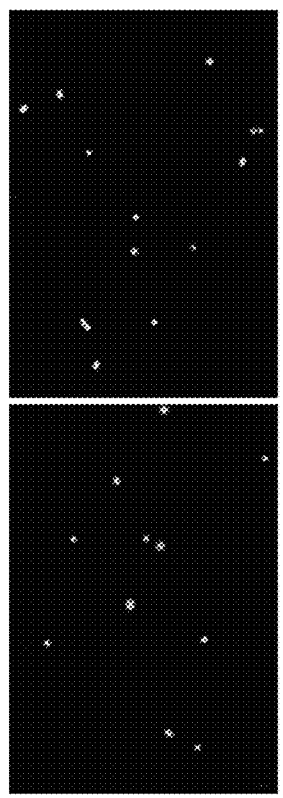 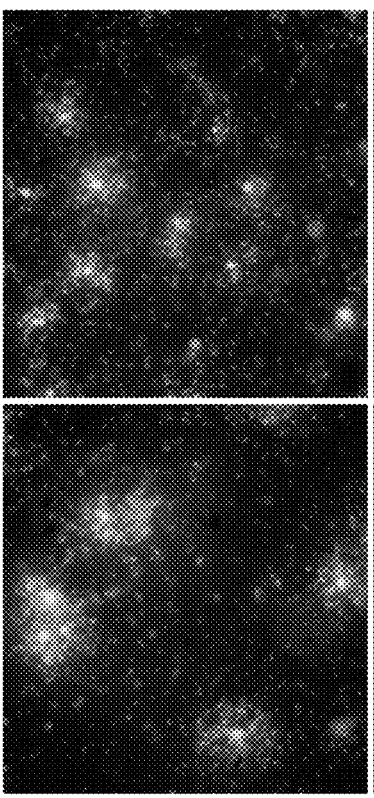 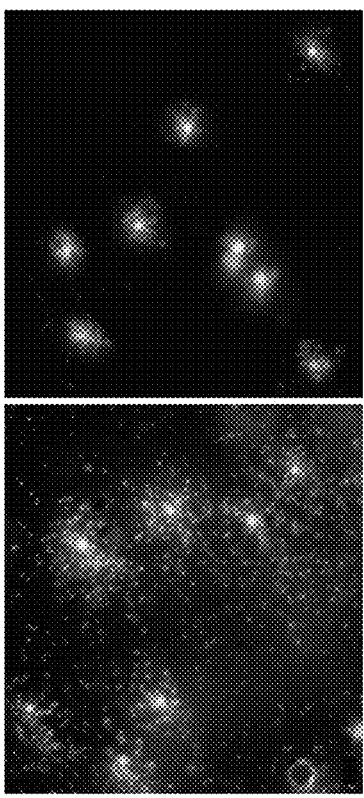
FIG. 16    FIG. 17    FIG. 18

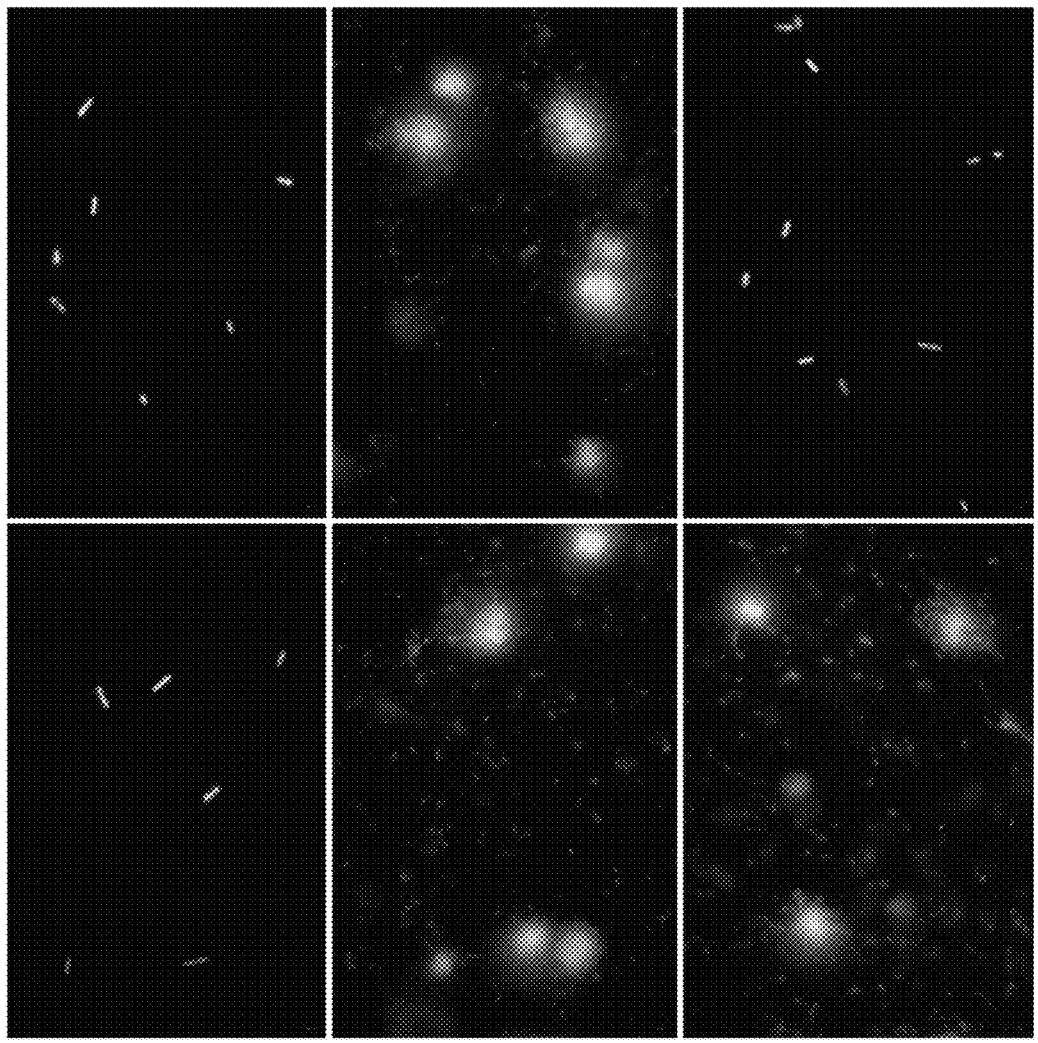

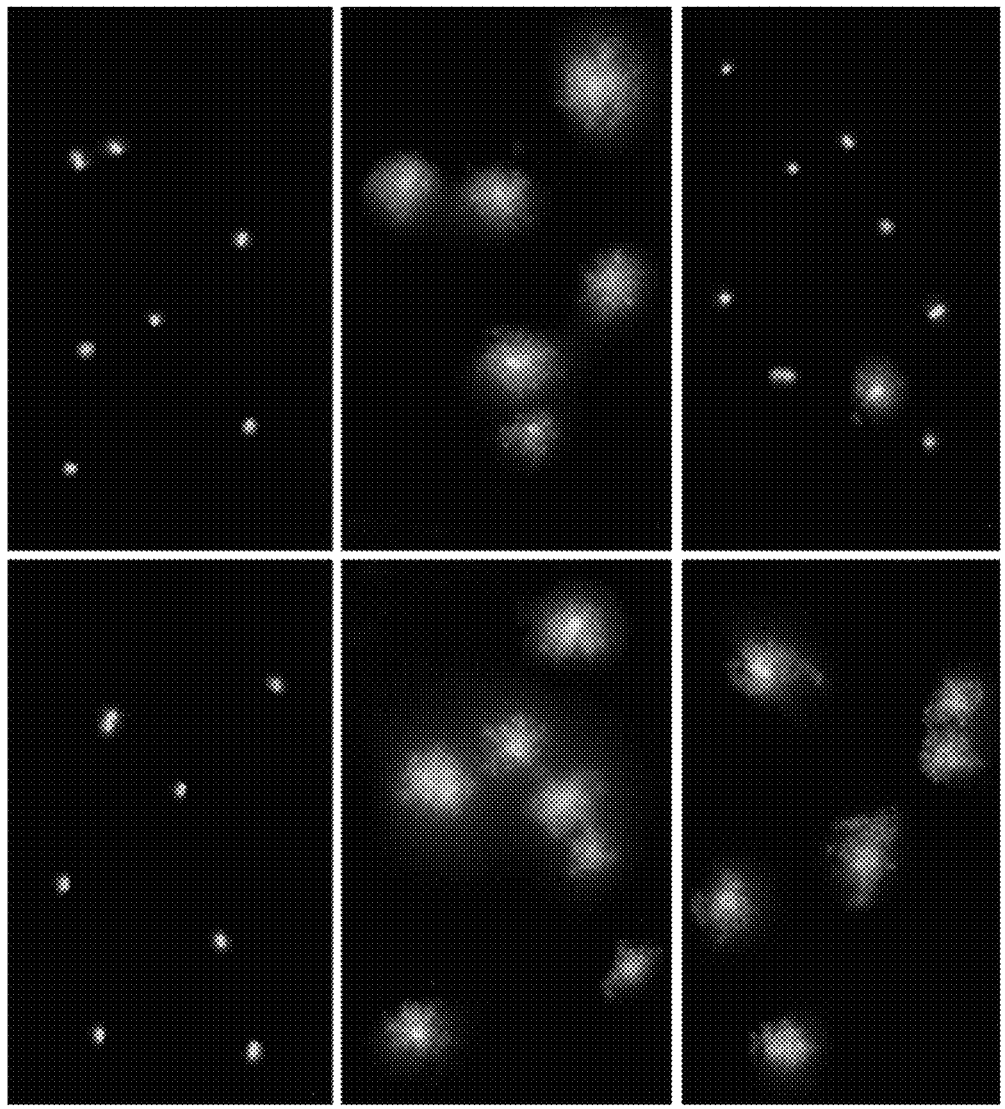

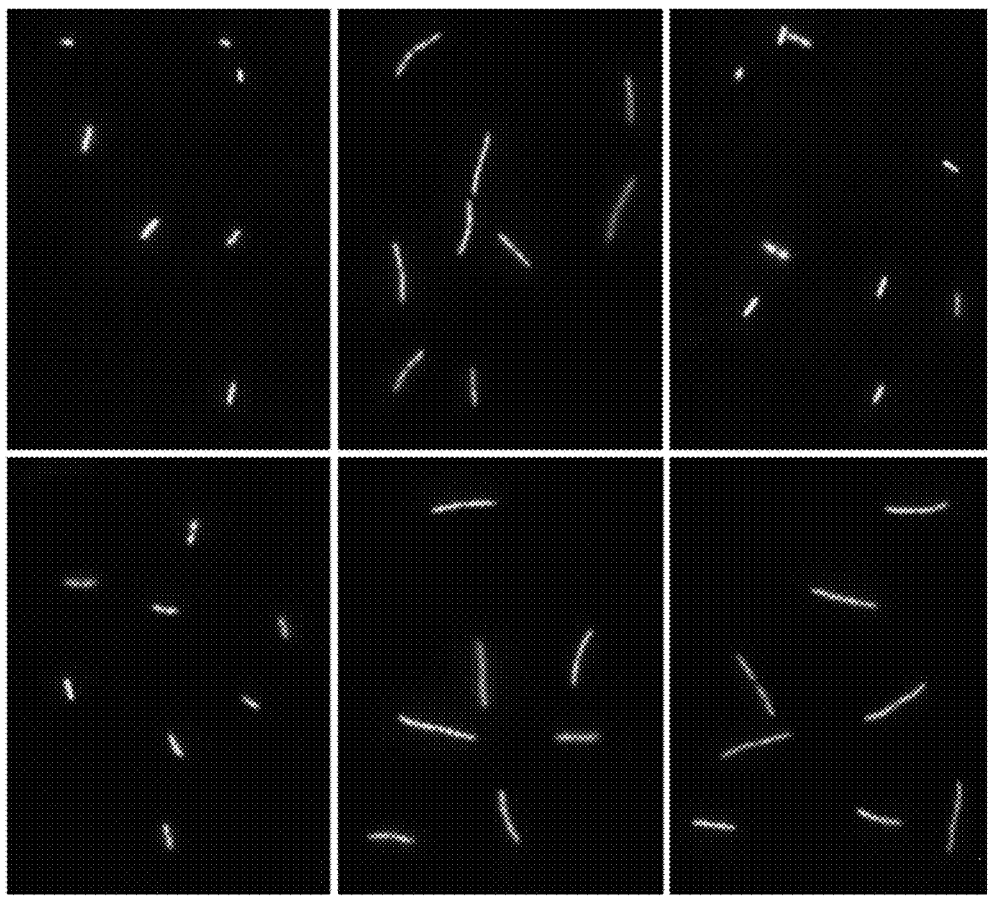

006f
PROCEDURE FOR THE RAPID DETERMINATION OF BACTERIAL SUSCEPTIBILITY TO ANTIBIOTICS THAT INHIBIT PROTEIN SYNTHESIS

This application is based on and claims the benefit of priority to European patent application 15382009.7, filed Jan. 21, 2015, the contents of which are incorporated herein by reference.

TECHNICAL FIELD

The present invention relates generally to the field of microbiology and the healthcare industry and more particularly relates to a methodology for the rapid evaluation of bacterial susceptibility or non-susceptibility to antibiotics that inhibit protein synthesis.

BACKGROUND

Pathogens resistant to multiple antibiotics present a continually increasing health risk, particularly in clinical settings. Patients may acquire infections through intrusive, but necessary, medical means, such as infections in the respiratory pathway during mechanical ventilation, in the urinary tract or blood vessels via catheters or even through skin wounds, such as incisions required for any number of medical procedures. Immunocompromised patients and patients located in Intensive Care Units (ICUs) are at increased risk of acquiring nosocomial infectious diseases which may be resistant to one or more antibiotics. For a variety of reasons, such infections may be associated with a high mortality rate. Previously, the European Center for Disease Control (ECDC) reported 25,000 annual deaths due to multi-resistant pathogens.

Well-selected, early antibiotic treatments provide the best defense against such multi-resistant pathogens. Given the high prevalence of resistances, current procedures require a bacterial culture for identification of the microorganism followed by an antibiogram, which routinely requires 2-3 days of bacterial growth. The step of culturing bacteria to construct an antibiogram alone generally requires about one day of incubation, or about a minimum of 18 hours.

Given the relative long time necessary to perform standard antibiogram, antibiotics are usually empirically provided at the onset. This first line of defense often relies on antibiotics generally known to be effective based on the likely pathogen involved. However, such treatments may be ineffective in 20-40% of cases, and a change of antibiotics later may have a reduced probability of success. Even educated assumptions may contribute to antibiotic misuse or overuse resulting in increasingly resistant strains of bacteria while the results of an antibiogram are pending.

The antibiogram results from clinical testing of isolated bacteria strains in vitro for bacterial susceptibility to antibiotics. A common methodology for constructing an antibiogram based on diffusion is the Kirby-Bauer method (Bauer A W, Kirby W M M, Sherris J C, Turck M *Antibiotic susceptibility testing by a standardized single disc method. Am J Clin Pathol* 1966; 45:493-496). In the semi-quantitative Kirby-Bauer method, several discs containing different antibiotics are placed in different zones of nutrient rich bacteria culture. Because the antibiotic diffuses into the agar away from the disc, the diameter around the disc in which bacteria does not grow is suggestive of the minimum inhibitory concentration (MIC) of that antibiotic to the cultured strain of bacteria.

A quantitative method may rely on dilution in a series of broths or agar solutions having progressively lower concentrations of the antibiotic in question. The lowest concentration of antibiotic in which the bacteria cannot grow provides the minimum inhibitory concentration of that antibiotic to the tested strain of bacteria. This quantitative method may be routinely employed in the hospitals, usually using commercial panels of antibiotics and semi-automated systems of incubation and software for data interpretation like the MicroScan WalkAway™ (Siemens), Phoenix (Becton Dickinson), or Vitek™ 2 (bioMérieux). With such growth-dependent automated systems, results of susceptibility or resistance to antimicrobians from a specific microorganism may be obtained in around 6-9 hours.

Each of the diffusion and the dilution methods rely on the principal of inhibiting bacterial proliferation in a nutrient rich medium and this requires sufficient time for many reproductive cycles of bacteria. As such, both methodologies may require a minimum of between 18 hours and 24 hours. It can be understood, conventional testing such as antibiograms fails to address the problems described above.

Additionally, a number of experimental approaches have been attempted with the goal of achieving faster susceptibility-resistance determinations. However, those experimental approaches failed to supplant the conventional, time consuming antibiogram. Accordingly, a need still exists for susceptibility testing capable of rapidly determining an antibiotic treatment enabling the rapid, effective administration of effective antibiotic treatments and reducing the misuse or overuse of antibiotics.

SUMMARY OF INVENTION

One embodiment of the invention relates to a method of rapidly evaluating the susceptibility of bacterial strains to a protein synthesis inhibiting antibiotic. The method may include the step of incubating a first portion of the strain of bacteria with a protein synthesis inhibiting antibiotic and adding an agent selected to induce a bacterial response which depends on or is influenced by protein synthesis. A second portion of the strain of bacteria may also be incubated with the agent selected to induce a bacterial response which depends on, or is influenced by, protein synthesis. The bacterial response in the first portion and the second portion of the strain of bacteria may then be evaluated and the strain of bacteria may be classified as susceptible or not susceptible to the protein synthesis inhibiting antibiotic based on the evaluation of the first and second portions of the strain of bacteria.

BRIEF DESCRIPTION OF DRAWINGS

FIG. 13 depicts an image of nucleoids from *Staphylococcus aureus* obtained with a Micromax assay in Example 3.

FIG. 14 depicts an image of nucleoids from *Staphylococcus aureus* obtained with a Micromax assay in Example 3.

FIG. 15 depicts an image of nucleoids from *Staphylococcus aureus* obtained with a Micromax assay in Example 3.

FIG. 16 depicts an image of nucleoids from *Staphylococcus aureus* obtained with a Micromax assay in Example 3.

FIG. 17 depicts an image of nucleoids from *Staphylococcus aureus* obtained with a Micromax assay in Example 3.

FIG. 18 depicts an image of nucleoids from *Staphylococcus aureus* obtained with a Micromax assay in Example 3.

FIG. 19 depicts an images of nucleoids from *Pseudomonas aeruginosa* obtained with a Micromax assay in Example 5.

FIG. 20 depicts an images of nucleoids from *Pseudomonas aeruginosa* obtained with a Micromax assay in Example 5.

FIG. 21 depicts an images of nucleoids from *Pseudomonas aeruginosa* obtained with a Micromax assay in Example 5.

FIG. 22 depicts an images of nucleoids from *Pseudomonas aeruginosa* obtained with a Micromax assay in Example 5.

FIG. 23 depicts an images of nucleoids from *Pseudomonas aeruginosa* obtained with a Micromax assay in Example 5.

FIG. 24 depicts an images of nucleoids from *Pseudomonas aeruginosa* obtained with a Micromax assay in Example 5.

FIG. 25 depicts an image of nucleoids from *Enterococcus faecalis* obtained with a variant Micromax assay in Example 6.

FIG. 26 depicts an image of nucleoids from *Enterococcus faecalis* obtained with a variant Micromax assay in Example 6.

FIG. 27 depicts an image of nucleoids from *Enterococcus faecalis* obtained with a variant Micromax assay in Example 6.

FIG. 28 depicts an image of nucleoids from *Enterococcus faecalis* obtained with a variant Micromax assay in Example 6.

FIG. 29 depicts an image of nucleoids from *Enterococcus faecalis* obtained with a variant Micromax assay in Example 6.

FIG. 30 depicts an image of nucleoids from *Enterococcus faecalis* obtained with a variant Micromax assay in Example 6.

FIG. 31 depicts and images of *Pseudomonas aeruginosa* obtained with a variant Micromax assay in Example 7.

FIG. 32 depicts an images of *Pseudomonas aeruginosa* obtained with a variant Micromax assay in Example 7.

FIG. 33 depicts an images of *Pseudomonas aeruginosa* obtained with a variant Micromax assay in Example 7.

FIG. 34 depicts an images of *Pseudomonas aeruginosa* obtained with a variant Micromax assay in Example 7.

FIG. 35 depicts an images of *Pseudomonas aeruginosa* obtained with a variant Micromax assay in Example 7.

FIG. 36 depicts an images of *Pseudomonas aeruginosa* obtained with a variant Micromax assay in Example 7.

Figures 1, 2, 3, 4, 5, 6:
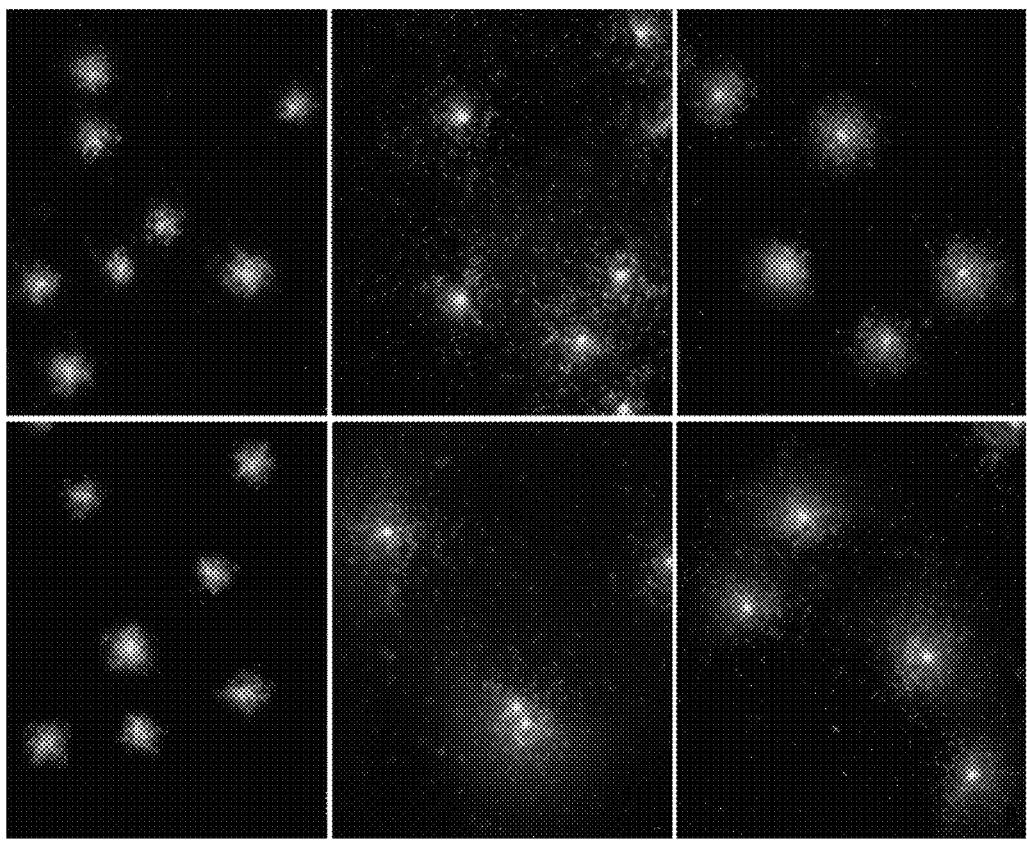
FIG. 1 depicts an image of nucleoids from *Escherichia coli* obtained with a Micromax assay in Example 1.
FIG. 2 depicts an image of nucleoids from *Escherichia coli* obtained with a Micromax assay in Example 1.
FIG. 3 depicts an image of nucleoids from *Escherichia coli* obtained with a Micromax assay in Example 1.
FIG. 4 depicts an image of nucleoids from *Escherichia coli* obtained with a Micromax assay in Example 1.
FIG. 5 depicts an image of nucleoids from *Escherichia coli* obtained with a Micromax assay in Example 1.
FIG. 6 depicts an image of nucleoids from *Escherichia coli* obtained with a Micromax assay in Example 1.

While the present invention may be embodied with various modifications and alternative forms, specific embodiments are illustrated in the figures and described herein by way of illustrative examples. It should be understood the figures and detailed description are not intended to limit the scope of the invention to the particular form disclosed, but that all modifications, alternatives, and equivalents falling within the spirit and scope of the claims are intended to be covered.

DETAILED DESCRIPTION OF INVENTION

Certain embodiments of the present invention allow for the rapid determination of bacterial susceptibility or resistance to antibiotics, particularly antibiotics which inhibit bacterial protein synthesis. As a non-limiting example, a number of antibiotics that inhibit bacterial protein synthesis are described in Lambert T, *Antibiotics that affect the ribosome. Rev Sci Tech Off Int Epiz* 2012 31: 57-64. Such antibiotics may be tested rapidly in accordance with embodiments described herein. These antibiotics affect bacterial cell wall by interacting with ribosomes, the organules where proteins are synthesized. The bacterial ribosomes are ribonucleoprotein complexes assembled in two big subunits, 30S and 50S.

Examples of antibiotics families which inhibit protein synthesizing include Oxazolinidones which prevent the formation of the initiation complex. Oxazolinidones seem to bind to the 23S rRNA V domain of 50S ribosomal subunit and to occupy the Aminoacyl (A) site of the 50S ribosomal subunit, inducing a conformational change that prevents tRNA from entering the site and forcing tRNA to separate from the ribosome. Oxazolinidones which may be tested in accordance with certain embodiments of the present invention include: eperezolid, linezolid, posizolid, radezolid, ranbezolid, sutezolid, tedizolid, and others.

Additional protein synthesis inhibiting antibiotics include tetracyclines and glycylcyclines (tigecycline), which bind to the 30S ribosomal subunit, preventing the entry of the aminoacyl transfer (t) RNAs to the Aminoacyl (A) site of the ribosome which is blocked by the antibiotic. A non-exhaustive list of tetracyclines which may be tested in accordance with certain embodiments of the present invention include: doxycycline, chlortetracycline, clomocycline, demeclocycline, lymecycline, meclocycline, metacycline, minocycline, oxytetracycline, penimepicycline, rolitetracycline, tetracycline and others.

Yet another family of protein synthesis inhibiting antibiotics includes aminoglycosides such as: tobramycin, streptomycin, dihydrostreptomycin, gentamicin, kanamycin, amikacin, arbekacin, bekanamycin, dibekacin, neomycin, framycetin, paromomycin, ribstamycin, netilmicin, sisomucin, isepamicin, verdamcin, astromicin, hygromycin B and others. Aminoglycosides affecting initiation, elongation and termination of protein synthesis increasing the error rate with premature termination of the peptidyl chain and also affect ribosomal translocation. They bind to the 30S subunit, specifically to the 16S ribosomal(r)RNA and the decoding A-site for the 4,6-substituted 2-deoxystreptamine (2-DOS).

Still more families of protein synthesis inhibiting antibiotics include macrolides, lincosamides, phenicols (chloramphenicol), streptogramins, and pleuromutilins and quinupristin/dalfopristin which block the peptidyl transfer step of peptide elongation on the 50S subunit. They bind to the 23S rRNA component of the 50S ribosome close to the peptidyl transferase centre (i.e domain V of the 23S rRNA), blocking the elongation of the peptide chain causing premature termination and leading to premature dissociation of the peptidyl-tRNA from the ribosome. Pleuromutilins bind to the peptidyl transferase centre, as well as phenicols. These latter bind specifically to the nucleotides within the central loop of domain V of the 23S rRNA. Ribosomal proteins L16 and the peptidyl (P)-site also participate in the binding. Orthosomycins also inhibit translation by binding to the 50S ribosomal subunit. Macrolides which may be tested in accordance with various embodiments of the present invention include: azithromycin, clarithromycin, dirithromycin, erythromycin, flurithromycin, josamycin, midecamycin, miocamycin, oleandomycin, rokitamycin, roxithromycin, spiramycin, troleandomycin, tylosin, ketolides, telithromycin, cethromycin, solithromycin and others. Lincosamides which may be tested in accordance with various embodiments of the present invention include: clindamycin, lincomycin, pirlimycin, and others. Streptogramins which may be tested in accordance with various embodiments of the present invention include: pristinamycin, quinupristin/dalfopristin, virginamicin, and others. Pleuromutilins which may be tested in accordance with various embodiments of the present invention include: retapamulin, tiamulin, valnemulin, and others. The amphenicol family of antibiotics including chloramphenicol, azidamfenicol, thiamphenicol, florfenicol and others may also be tested with certain embodiments of the present invention.

Additionally, Fusidic acid prohibits protein synthesis by preventing the turnover of elongation factor G (EF-G) in the ribosome.

Retapamulin and mupirocin may also inhibit protein synthesis, but their precise mechanism is unknown.

Additional antibiotics that inhibit protein synthesis envisioned for use with certain embodiments described herein include those antibiotics which inhibit the peptide deformylase.

Bacterial resistant to antibiotics that inhibit bacterial protein synthesis manifests by a number of mechanisms Lambert T *Antibiotics that affect the ribosome. Rev Sci Tech Off Int Epiz* 2012 31: 57-64.

One mechanism by which bacteria may exhibit a resistance to protein synthesis inhibiting bacteria is by enzymatic inactivation. Detoxification enzymes, mainly encoded by genes from plasmids or transposons, may metabolize antibiotics like aminoglycosides, erythromycin, lincosamides, chloramphenicol and streptogramins, thereby limiting their antibacterial efficacy.

Another bacterial mechanism which exhibits a resistance to protein synthesis inhibiting bacteria is target alteration. Mutations may affect the rRNAs (e.g. 16S rRNA or 23S rRNA) or ribosomal proteins (e.g. S12 to streptomycin, L4 and L22 to macrolides) involved in antibiotic binding. Moreover, methyltransferases may also affect targets. For example, the 23S rRNA may be methylated in adenine 2058 by Erm enzymes, constitutive or inducible, leading to resistance to macrolides. They are mostly borne by mobile elements, representing a potential risk of dissemination. Monomethylation results in low level resistance to erythromycin whereas dimethylation confers high resistance.

Additionally, Ribosomal protection proteins, homologues to the elongation factors, confer resistance to tetracyclines possibly preventing protein synthesis inhibiting antibacterial activity.

Yet another mechanism by which bacteria may resist protein synthesis inhibiting antibiotics is by impaired uptake. Impermeable or energy dependent efflux systems reduce the intracellular concentration of the antibiotic and may produce a moderate resistance to aminoglycosides, and specifically to tetracyclines in gram-negative bacteria.

Certain embodiments described herein provide a means for rapidly determining whether bacteria is susceptible or non-susceptible in relation to antibiotics being tested. The term "susceptible" should be understood to correspond to the CLSI definition, for example a susceptible microorganism exhibits a level of antimicrobial activity associated with a high likelihood of therapeutic success. As used herein, the term "non-susceptible" refers to those microorganisms which are not determined to be susceptible. In practice, this definition encompasses the CLSI indications of both resistant and intermediate microorganisms.

Whereas, some previous rapid susceptibility detection methods relied on the rapid growth in the individual cell size of small numbers of bacteria, certain protein synthesis inhibiting antibiotics may prevent this growth which may present a false positive for resistant bacteria under certain conditions.

In accordance with certain embodiments of the present invention, a bacterial response is induced which depends on or is influenced by protein synthesis. Bacterial resistance to protein synthesis inhibiting antibiotics can be evaluated through the antibiotics ability to supress the bacterial response. For the purposes of this disclosure a "bacterial response" should be understood to be a chemical, biological, genetic, or physical change to bacteria at the DNA level, a cellular component level, or at the cellular level. In some embodiments, the bacterial response is directly, or indirectly discernible, such as through the use of assays, microfluidic devices, or by other measurement and/or testing protocols known to those of skill in the art.

Examples of bacterial responses at the DNA level include DNA damage and DNA fragmentation. In particular, DNA damage or fragmentation which is at least partially dependent on protein synthesis may indicate of the effectiveness of protein synthesis inhibiting antibiotics. As non-limiting examples, this DNA fragmentation, which is at least partially dependant on protein synthesis may be induced in some bacteria by exposure to quinolones (e.g. norofloxin, ciproflaxin, moxifloxacin, and others). Since all quinolones produce a similar response in gram negative bacteria, namely DNA fragmentation, quinolones are expected to work well as an agent for inducing a bacterial response. While this is the case for at least most gram negative bacteria, resistance to quinolones is possible, and in such strains a susceptibility determination can't be made with respect to the protein synthesis inhibiting antibiotic.

A bacterial response in the form of DNA fragmentation may be induced with mitomycin C. Mitomycin C presents a robust agent for inducing bacterial response, because at present, there does not appear to be any natural bacterial resistances to mitomycin C. Mitomycin C appears to produce protein synthesis dependant responses in at least *E. coli, K. pneumonia, P. aeruginosa*, and *A. baumannii* and is expected to produce a bacterial response in most gram negative bacteria.

In other embodiments, DNA fragmentation which depends on protein synthesis may be indirectly produced, such as by lysostaphin which partially digests bacterial cell walls after a short exposure causing the release significant quantities of deoxyribonuclease (DNase). DNase is an enzyme which, when released from the bacterial cell wall results in DNA fragmentation in a manner which depends on protein synthesis. As another example, DNA fragmentation can be induced by incubating bacteria with surfactants and/or enzymes that effect bacteria cell walls in a manner that depends on protein synthesis and which promote autolysis. Autolysis in certain bacteria may be induced by incubation with bile, deoxycholate, Triton X-100, as well as peptidoglycan digesting enzyme lysozyme and antibiotic inhibitors of peptidoglycan synthesis.

In certain further embodiments, the bacterial response of DNA damage may be induced by alkykating agents. A non-exhaustive list of alkykating agents may include: nitrogen mustards, such as cyclophosphamide, mechlorethamide, uramustine, melphalan, chlorambucil, ifosfamide, bendamustine; diepoxybutane; carzinophilin/azinomycin B; sandramycin, luzopeptins, and isochrysohermidin; biselezin, pyrrolobenzodiazepine dimers; dinuclear cis-DDP analogues; psoralens; cyclophosphamide, pyrrolizide alkaloids; and others. Perhaps even "alkylating-like" agents, such as platinums, or platinum analogues, may be employed to induce a bacterial response. Alkylating-like agents may include cisplatin, carboplatin, nedaplatin, oxalipatin, satraplatin, or triplatin tetranitrate.

Examples of bacterial responses at the cellular component level may include cell wall damage, which may be caused by agents that inhibit peptidoglycan synthesis or even cause peptidoglycan digestion. The beta-lactams family of antibiotics may be employed for inducing cell wall damage in a manner which depends on protein synthesis. As non-limiting examples, beta-lactams contemplated for possible use include penicillins (penems), cephalosporins (cephems), carbapenems. Beta-lactams have demonstrated effectiveness in inducing bacterial response in a number of bacterial species, gram negative strains of bacteria being the most widely tested. However, beta-lactams can only be effective as an agent for inducing a bacterial response in strains of bacteria which are not themselves resistant to beta-lactams.

Additional families of antibiotics to induce this bacterial response may include cycloserine, fosfomycin, bacitracin, and glycopeptides. Cell wall lysis, or peptidoglycan digestion may be induced with lysozyme. Because most bacteria have peptidoglycan, Lysozyme is expected to provide a useful agent for inducing a bacterial response in both gram negative and gram positive bacteria.

Examples of bacterial responses at the cellular level includes changes in cell appearance, such as cell size, or cell enlargement. In particular, various antibiotics and DNA damaging or toxic agents may induce cell enlargement in a manner which depends on, or is influenced by, protein synthesis.

It may be appreciated that bacterial responses can occur on multiple levels simultaneously, sequentially, or in overlapping intervals. Additionally, certain agents described may be capable of inducing bacterial responses on multiple levels. In the examples which follow, the bacterial response may be described in terms of the bacterial response which is monitored by assays or other means. In some instances, the concentration of the agent employed can affect the type of bacterial response which is induced.

In certain embodiments, a bacterial response is induced in bacteria, such as in a strain of bacteria or in a sample of bacteria. As a non-limiting example, a bacteria sample may be generated in a clinical setting by known culturing methods for isolating and identifying bacteria. The agent inducing this bacterial response may be induced in two separated portions of the bacteria, such as a first portion and a second portion. The portions may be separated spatially, such as within the same petri dish or other incubation container, or they may be physically separated, such as in separated petri dishes or incubation containers. Regardless of the manner in which the first portion and the second portion are separated, it may be appreciated that the designation of a "first" and a "second" portion may be considered arbitrary with respect to location or spacing, except to the extent the portions are separated sufficiently for incubation under differing conditions. Additionally, the designation of a "first" and a "second" portion may be arbitrary with respect to the timing of any incubation. The first and second portions may be incubated with their respective treatments simultaneously, one after the other, or in a staggered manner. As a non-limiting example, the start of multiple treatments may be staggered in a manner which causes those treatments to be completed at or around the same time.

In one embodiment, both portions are subjected to an agent which induces a bacterial response. In particular, the induced bacterial response is one that either depends on the synthesis of proteins or which is influenced by the protein synthesis. One of the first and second portions are exposed to the protein synthesis inhibiting antibiotic and the other is not. In some embodiments, one of the portions of the bacterial strain are exposed to the protein synthesis inhibiting antibiotic prior to incubation with the agent for inducing a bacterial response. In some embodiments, the protein synthesis inhibiting antibiotic is introduced in dosages which are recognized as susceptibility and/or resistance break points. For example, International organizations like the Clinical and Laboratory Standards Institute (CLSI) establish the breakpoint concentration of susceptibility or resistance for each antibiotic and microorganism. Susceptibility of a bacteria to an antibiotic may be understood in some cases with reference to a minimum inhibitory concentration (MIC), i.e. the lowest dose of the antibiotic which significantly inhibits bacterial cell growth.

In some embodiments, an additional treatment is applied to a portion of the bacterial strain, which may be separated from the first and second portions. This portion may be arbitrarily considered a third portion and may be incubated with the protein synthesis inhibiting protein, but without inducing the bacterial response. In some cases, this additional treatment may serve as a control for comparison with the treatments of the first and the second portions. This control allows for a determination as to whether the protein synthesis inhibiting antibiotic itself induces any cell changes making the bacterial response more difficult to determine.

In a further embodiment, an additional treatment may be applied to another portion of the bacterial strain which may be separated spatially and/or physically from the other portions. This portion may remain free from the agent which induces the bacterial response and free from the protein synthesis inhibiting antibiotic and may serve as a control. This portion may be arbitrarily considered a fourth portion which may be employed in conjunction with the first and second portions or in conjunction with the first, second and third portions. As one example, the fourth portion may serve as a control providing baseline information regarding DNA fragmentation or perhaps even cell size. The fourth portion may provide a baseline for comparison with the portion subjected to only the bacterial response inducing agent. In the event there is no significant differences, the bacteria may be resistant to the agent selected to induce the bacterial response.

Rapid Determination of Susceptibility or Non-Susceptibility to Antibiotics that Inhibit Protein Synthesis—Evaluating Responses at the DNA Level.

Example 1

As an exemplification of the principals previously described, two strains of Escherichia coli exponentially growing in Mueller-Hinton broth were assayed (FIGS. 1-6). The first strain of Escherichia coli was a TG1 strain susceptible to both the aminoglycoside tobramycin (an inhibitor of protein synthesis) and the quinolone ciprofloxacin (an agent which induces DNA fragmentation by trapping of topoisomerases in DNA) (FIGS. 1-3). The second strain was a clinical isolate resistant to tobramycin and susceptible to ciprofloxacin (FIGS. 4-6). Four treatments were applied to each strain to rapidly distinguish the susceptible and the resistant strain to tobramycin.

One portion of both bacterial strains was incubated with tobramycin at 4 µg/ml for 40 minutes (FIGS. 1 and 4), a dosage indicated by the CLSI as the breakpoint of susceptibility to tobramycin in the standard antibiogram based on microdilution. Another portion of both strains was incubated with ciprofloxacin at 1 µg/ml for 30 min (FIGS. 2 and 5). Still another portion of both strains was incubated with tobramycin at 4 µg/ml for 10 min followed by ciprofloxacin at 1 µg/ml for 30 min, without removing the tobramycin (FIGS. 3 and 6). A final portion was left with no antibiotic.

After each incubation cells were processed using the variant of the Micromax technology to visualize the nucleoids, i.e. bacterial chromosomal DNA, in all the cells of the population. Cells from each culture were immersed in an agarose microgel on a slide and incubated with a specific lysing solution to remove the cell wall in all the cells and release in the microgel the nucleoids contained inside the bacteria. These are dried, stained with a high sensitive fluorochrome for DNA like SYBR Gold and visualized under fluorescence microscopy. FIGS. 1-6 depicts representative images captured under each of the conditions described below.

As can be seen in FIGS. 1 and 4, those cells incubated with tobramycin, the antibiotic that inhibits the synthesis of proteins, did not result in any modifications of the nucleoids. These results were similar in appearance to those from the cultures without any antibiotics in both susceptible and resistant strains to tobramycin.

Those cells incubated with ciprofloxacin alone demonstrated nucleoids with extensive fragmented DNA, as expected, since both strains are susceptible to the quinolone, seen in FIGS. 2 and 4.

Those cells incubated with tobramycin followed by ciprofloxacin demonstrated nucleoids with reduced level of DNA fragmentation in the strain susceptible to tobramycin, FIG. 3. In the resistant strain of bacteria, the DNA was extensively fragmented, similarly to those from the culture incubated with ciprofloxacin only, in the strain resistant to tobramycin, FIG. 6.

FIGS. 1-6 illustrate that a tobramycin pre-incubation significantly reduces the DNA fragmentation level caused by ciprofloxacin in the tobramycin-susceptible strain FIG. 3, whereas this decreasing effect is not evident in the tobramycin-resistant strain. Like FIG. 5, a large extent of DNA fragmentation is seen in FIG. 6.

The above described methodology was employed to rapidly determine the susceptibility of 12 strains of E. coli to tobramycin. One portion of each bacterial strain was incubated with tobramycin at the susceptibility breakpoint dosage, 4 µg/ml, for 40 min. A portion of each strain was incubated with ciprofloxacin at 1 µg/ml for 30 min. Still another portion of each strain was incubated with tobramycin at 4 µg/ml for 10 min followed by ciprofloxacin at 1 µg/ml for 30 min, without removing the tobramycin. A final portion of each strain was left with no antibiotic. E. coli strains were identified as susceptible or not based on the levels of DNA fragmentation in the portion of each strain incubated with ciprofloxacin and the portion incubated with tobramycin and ciprofloxacin.

By comparing assayed strains for the amount of DNA fragmentation, this methodology identified nine of the twelve strains as susceptible to tobramycin and three of the twelve strains as non-susceptible. A standard antibiogram obtained by microdilution was performed on the same strains and a comparison between the results indicated the same nine strains as susceptible and the same three strains as non-susceptible (resistant) according to the MIC-CLSI criterion (breakpoint of susceptibility ≤4 µg/ml) were successfully identified by the rapid test.

It can be understood, DNA fragmentation by ciprofloxacin is at least partially dependent on protein synthesis. If protein synthesis is successfully inhibited by tobramycin (i.e. in the strain susceptible to tobramycin), the DNA fragmentation by ciprofloxacin is decreased. If the protein synthesis is not successfully inhibited by tobramycin (i.e. in the strain resistant (non-susceptible) to tobramycin), the DNA fragmentation by ciprofloxacin remains massive, unchanged. This distinction provides a means for determining susceptible and non-susceptible strains. Importantly, this distinction can be rapidly discriminated in an assay.

The principals exemplified in Example 1 were confirmed with the aminoglycoside amikacin. Briefly, a susceptible and resistant strain of E. coli were exposed to similar conditions to those described in Example 1, except that amikacin was utilized as the protein synthesis inhibiting antibiotic. Specifically, each was strain subjected to four treatments. One portion received no antibiotics, and another portion received only a quinolone, such as ciprofloxacin or norfloxacin to induce DNA fragmentation. Still another portion received the protein synthesis inhibiting antibiotic aminoglycoside amikacin, followed by the quinolone. Another portion received only amikacin. A final portion received neither antibiotic. The susceptibility of E. coli to amikacin was successfully determined through the above described methodology.

The principals exemplified in Example 1 were further confirmed with the aminoglycoside gentamicin. Briefly, the rapid test was performed on 15 isolated E. coli strains according to the methodology described above, except that gentamicinin was utilized as the protein synthesis inhibiting antibiotic. Suppressed DNA fragmentation were used to characterize bacterial susceptibility and those characterizations were verified with the standard antibiogram for gentamicin by microdilution. The results correlated perfectly and the 10 susceptible strains and the 5 resistant (non-susceptible) strains to gentamicin were all unambiguously identified with the rapid test. Similar results were additionally achieved with chloramphenicol as inhibitor of protein synthesis and the quinolone ciprofloxacin.

Example 2

DNA damage or DNA fragmentation induced by mitomycin C has been found partially dependent on protein synthesis. Mitomycin C is an alkylating agent that reacts with the guanine nucleoside sequence 5'-CpG-3'. It inhibits DNA replication by covalently reacting with DNA, forming crosslinks between complementary strands of DNA. Bacterial DNA fragmentation may occur secondarily as a consequence of DNA repair and the activation of the SOS response or during the cell death process. Bacterial susceptibility to protein synthesis inhibiting antibiotics may be determined utilizing mitomycin C as an agent which induces DNA damage or DNA fragmentation.

Mitomycin C may present a robust agent for inducing DNA fragmentation or DNA damage in bacteria because no significant resistances to mitomycin C are expected, unlike antibiotics such as quinolones or inhibitors of cell wall synthesis described previously. For this reason, mitomycin C may have a more expanded application to many bacterial species and strains.

Bacteria may be incubated with an antibiotic that inhibits protein synthesis prior to the addition of mitomycin C. If the bacterial strain is susceptible to the antibiotic that affects protein synthesis, the level of DNA fragmentation of the bacterial chromosome by the mitomycin C is reduced in comparison to that produced by incubation with mitomycin C alone. If the bacteria are resistant to the antibiotic that affects protein synthesis, the level of chromosomal DNA fragmentation by mitomycin C remains practically unchanged. The antibiotic cannot act, so protein synthesis is effective and the DNA is fragmented by mitomycin C as usual.

Figure 7:
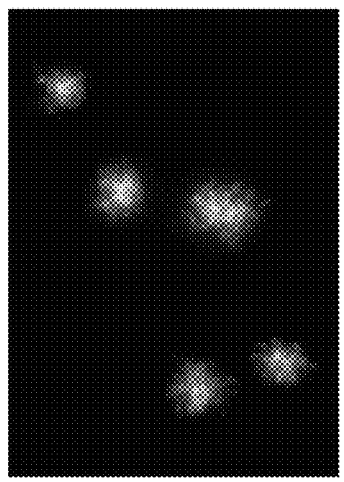
FIG. 7 depicts an image of nucleoids from *Escherichia coli* obtained with a Micromax assay in Example 2.
Figure 8:
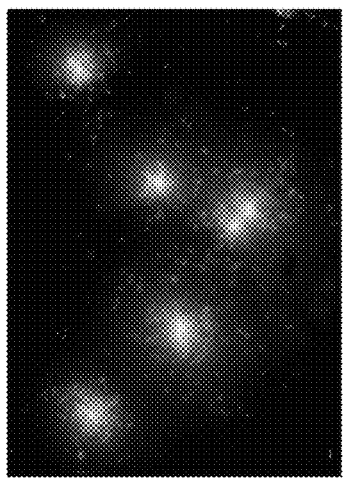
FIG. 8 depicts an image of nucleoids from *Escherichia coli* obtained with a Micromax assay in Example 2.
Figure 9:
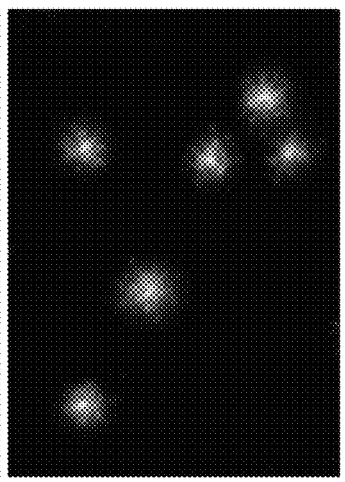
FIG. 9 depicts an image of nucleoids from *Escherichia coli* obtained with a Micromax assay in Example 2.

As an illustrative example, two strains of *Escherichia coli* exponentially growing in Mueller-Hinton broth were incubated under different treatments and then assayed, as seen in FIGS. 7-12. FIGS. 7-9 depict a TG1 strain susceptible to the aminoglycoside tobramycin, an inhibitor of protein synthesis, and mitomycin C, an agent which induces DNA damage. The other strain illustrated in FIGS. 10-12 was a clinical isolate resistant to tobramycin.

Figure 11:
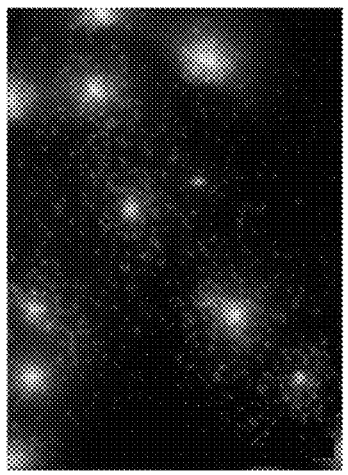
FIG. 11 depicts an image of nucleoids from *Escherichia coli* obtained with a Micromax assay in Example 2.
Figure 12:
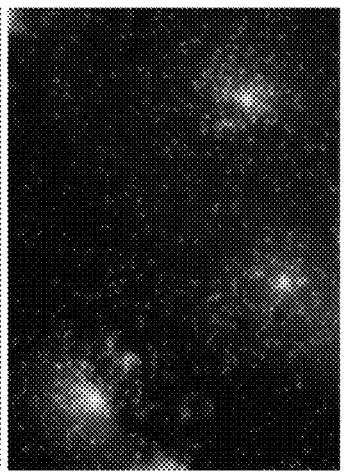
FIG. 12 depicts an image of nucleoids from *Escherichia coli* obtained with a Micromax assay in Example 2.

One portion of both bacterial strains was incubated with tobramycin at 4 µg/ml for 90 min (FIGS. 7 and 10), a dosage indicated by the CLSI as the breakpoint of susceptibility to tobramycin in the standard antibiogram based on microdilution. Another portion of both strains was incubated with mitomycin C at 50 µg/ml for 60 min (FIGS. 8 and 11). Still another portion of both strains was incubated with tobramycin at 4 µg/ml for 30 min followed by mitomycin C at 50 µg/ml for 60 min, without removing the tobramycin (FIGS. 9 and 12). A final portion was left with no antibiotic.

After incubation, cells were processed using a variant of the Micromax technology to visualize nucleoids, i.e. bacterial chromosomal DNA, in all the cells of the population. Samples from cells from the culture are immersed in an agarose microgel on a slide and incubated with a specific lysing solution to remove the cell wall in all the cells and release in the microgel the nucleoids contained inside the bacteria. These are dried, stained with a highly sensitive fluorochrome for DNA like SYBR Gold and visualized under fluorescence microscopy, Nucleoids from *E. coli* obtained using the Micromax assay are represented in FIGS. 7-12, FIGS. 7-9 correspond to a strain susceptible to tobramycin (TG1) and FIGS. 10-12 to a strain resistant to tobramycin.

Figure 10:
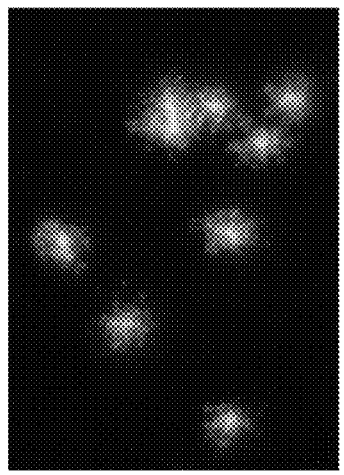
FIG. 10 depicts an image of nucleoids from *Escherichia coli* obtained with a Micromax assay in Example 2.

As can be seen in FIGS. 7 and 10, incubation with tobramycin, the antibiotic that inhibits the synthesis of proteins, does not result in modifications of the nucleoids which are similar in appearance to those from the cultures without antibiotics, in both susceptible and resistant strains to tobramycin.

FIGS. 8 and 11, demonstrate incubation with mitomycin C results in nucleoids with fragmented DNA in both strains, as expected. The DNA fragmentation level can be variable in the different nucleoids and in the different strains.

The assay depicted in FIG. 9 illustrates that incubation with tobramycin followed by mitomycin C resulted in nucleoids without observable DNA fragmentation in the strain susceptible to tobramycin. In contrast, FIG. 12 illustrates that in bacteria resistant to the protein inhibiting antibiotic (tobramycin in this case) the DNA remained fragmented, similarly to those from the culture incubated with mitomycin C only (FIG. 11).

From these results, it can be understood that DNA fragmentation by mitomycin C is partially dependent on protein synthesis and that if protein synthesis is successfully inhibited by tobramycin (i.e. in the strain susceptible to tobramycin), the DNA fragmentation by mitomycin C is decreased or suppressed. If on the other hand, protein synthesis is not successfully inhibited by tobramycin (i.e. in a non-susceptible strain), the DNA fragmentation by mitomycin C remains largely unchanged. The susceptible and the non-susceptible strains can be rapidly discriminated with the assay. Other agents that induce DNA damage could be used instead of mitomycin C. The list is numerous and includes mainly alkylating agents, many of them used in chemotherapy of cancer.

Example 3

In a further example, it has been found DNA damage or DNA fragmentation induced by deoxyribonuclease (DNase) released by cell wall lysis of *Staphylococcus aureus* is dependent on protein synthesis. *S. aureus* is a Gram positive bacterium which synthesizes and secretes DNase, which is stored at the cell wall. When the cell wall is partially digested by a short treatment with lysostaphin, the DNase is released resulting in DNA fragmentation. The DNA fragmentation may be visualized using the Micromax assay (Tamayo M, Santiso R, Gosalvez J, Bou G, Fernández M C, Fernández J L. *Cell wall active antibiotics reduce chromosomal DNA fragmentation by peptidoglycan hydrolysis in Staphylococcus aureus*. Arch Microbiol 2012; 194: 967-975). In one embodiment, bacteria are incubated with an antibiotic that affects protein synthesis prior to the addition of lysostaphin. If the bacterial strain is susceptible to the antibiotic that affects protein synthesis, the level of DNA fragmentation of the bacterial chromosome by the DNase is reduced or suppressed in comparison to that produced by incubation with the lysostaphin alone. DNase is an enzyme of protein nature, being synthesized at the ribosomes of *S. aureus*. Possibly, the amount of DNase synthesized is reduced by the antibiotic that inhibits protein synthesis, so the amount of DNase stored at the cell wall is decreased in comparison with the control cells untreated with the antibiotic that inhibits protein synthesis. In which case, lysostaphin releases a lower amount of DNase, so the DNA appears less fragmented. Otherwise, if the bacteria are non-susceptible with respect to the antibiotic that affects protein synthesis, the level of chromosomal DNA fragmentation by the DNase remains practically unchanged. The antibiotic cannot act, so protein synthesis is effective and the DNase production is not modified and the nucleoids are fragmented as usual.

In an exemplification of this principal, two strains of *S. aureus* growing in Mueller-Hinton agar with 5% sheep blood were assayed. One strain was susceptible to the macrolide azithromycin (an inhibitor of protein synthesis) (FIGS. 13-15) and the other strain was a clinical isolate resistant to azithromycin (FIGS. 16-18). The purpose was to rapidly distinguish susceptible and non-susceptible strains to azithromycin. Cultures were processed direct from standard growing agar plates 18-24 h and it was not necessary the cells being exponentially growing previously to the assay.

Each of these strain was subjected to four treatments. One portion of both strains was incubated with azithromycin at 2 μg/ml for 120 min; 2 μg/ml being indicated by the CLSI as the breakpoint of susceptibility to azithromycin. The cells were then lysed to release nucleoids and images of FIGS. 13 and 16 were generated. Another portion of each strain was incubated with lysostaphin at 10 μg/ml for 1 min. FIGS. 14 and 17 depict the nucleoids released in each strain for this treatment. Still another portion was incubated with Azithromycin at 2 μg/ml for 120 min followed by lysostaphin at 10 μg/ml for 1 min, without removing the azithromycin. The assays for these treatments can be seen at FIGS. 15 and 18. A final portion was left without either antibiotic.

After the incubation, the cells were processed using the variant of a Micromax technology to lyse cells with affected cell walls. As indicated previously, samples from cells from the culture are immersed in an agarose microgel on a slide and incubated with a specific lysing solution to remove the cell wall in those cells affected by lysostaphin and release in the microgel the nucleoids contained inside the bacteria. These are dried, stained with a highly sensitive fluorochrome for DNA like SYBR Gold and visualized under fluorescence microscopy.

As can be seen in FIGS. 13 and 16, incubation with azithromycin alone, the antibiotic that inhibits the synthesis of proteins, did not result in modification of the appearance of the bacteria. Each strain appears similar to those from the cultures without antibiotics, in both susceptible and resistant strains to azithromycin.

As can be seen in FIGS. 14 and 17, incubation with lysostaphin results in release of nucleoids with a large extent of DNA fragmentation as expected, due to the liberation of DNase.

Incubation with azithromycin followed by lysostaphin resulted in nucleoids with strongly reduced level of DNA fragmentation or even suppression of DNA fragmentation in the strain susceptible to azithromycin, seen in FIG. 15. In contrast, a large extend of DNA fragmentation, similar to those from the culture incubated with lysostaphin only (FIG. 17) is seen in the strain resistant to azithromycin (FIG. 18).

As such, DNA fragmentation by DNase released in *S. aureus* through digestion of the cell wall with lysostaphin is modulated by protein synthesis. If protein synthesis is successfully inhibited by azithromycin (i.e. in the strain susceptible to azithromycin), the DNase level stored at the cell wall is decreased, being liberated a lower level of DNase after cell wall digestion with lysostaphin, so the DNA fragmentation is decreased. But if the protein synthesis is not successfully inhibited by azithromycin (i.e. in the non-susceptible strain), the DNA fragmentation by DNase remains largely, unchanged. In this manner the susceptible and the non-susceptible strains can be rapidly discriminated with the assay.

Example 4

In another example, it has been determined that the DNA damage or fragmentation induced in the autolytic response of *Streptococcus pneumoniae* is dependent on protein synthesis. When the Gram positive *S. pneumoniae* (pneumococcus) is incubated with surfactants and/or enzymes that affect the cell wall, an enzymatic response is activated resulting in autolysis and DNA fragmentation. This is a response previously utilized as a test to identify *S. pneumoniae*. A bacterial response may be triggered by incubation with detergents like bile, deoxycholate or Triton X-100, as well as the peptidoglycan digesting enzyme lysozyme and antibiotics inhibitors of peptidoglycan synthesis, among others. The major autolysin activated is the N-acetylmuramoyl-L-alanine amidase (LytA) (Mellroth P, Daniels R, Eberhardt A, Rönnlund D, Blom H, Widengren J, Normark S, Henriques-Normark B. *Lyt A, major autolysin of Streptococcus pneumoniae, requires access to nascent peptidoglycan.* J Biol Chem 2012, 287: 11018-11029).

As a non-limiting example, the agent for inducing the autolytic response showing DNA fragmentation may include 0.05% Triton X-100, 2 mg/ml lysozyme, 25 mM EDTA, and may have an incubation time of about 5 min. EDTA may optionally be used in combination with the other agents for the purpose of improving the quality of the images. In one embodiment, the antibiotic that inhibits protein synthesis is provided prior to the addition of the Triton-lysozyme-EDTA treatment. If the bacteria are susceptible to the antibiotic that affects protein synthesis, protein synthesis is not effective and the frequency of cells lysed and showing DNA fragmentation is potently reduced in comparison to that produced by incubation with Triton-lysozyme-EDTA alone. On the other hand, if the bacteria are non-susceptible with respect to the antibiotic that affects protein synthesis, the proportion of cells lysed and showing chromosomal DNA fragmentation may be unchanged or only slightly reduced. The antibiotic cannot act, so protein synthesis is effective and the DNA is fragmented after the autolytic-induced treatment, as usual.

In an exemplification of this principal, two strains of *S. pneumoniae* growing in Mueller-Hinton II broth complemented with cations and 2-5% lysed horse blood, at 37° C. with 5% CO2, were assayed. One strain having an MIC of 0.25 μg/ml was susceptible and the other strain having an MIC>32 μg/ml was resistant to the macrolide azithromycin (inhibitor of protein synthesis). The purpose of the assay was to distinguish rapidly the susceptible and the resistant (i.e. non-susceptible) strain to azithromycin.

Each of these two strains were subjected to four treatments. A first portion of both strains was incubated with azithromycin at a concentration of 0.5 μg/ml for 60 min. The dose was that indicated by the CLSI as the breakpoint of susceptibility to azithromycin in the standard antibiogram based on microdilution. Another portion of both strains was incubated with 0.05% Triton X-100, 2 mg/ml lysozyme, 25 mM EDTA, 5 min. Still another portion of each strain was incubated with azithromycin at 0.5 μg/ml for 60 min followed by 0.05% Triton X-100, 2 mg/ml lysozyme, 25 mM EDTA, 5 min, without removing the azithromycin. A final portion of each strain remained without any antibiotics.

After incubation cells were processed using the variant of the Micromax technology to visualize the nucleoids. In the same manner indicated previously, samples from cells from the culture are immersed in an agarose microgel on a slide and incubated with a specific lysing solution to remove the cell wall in all the cells and release in the microgel the nucleoids contained inside the bacteria. Whereas incubation is generally five minutes, in this case two minutes at room temperature proved enough. The microgels are dried, stained with a high sensitive fluorochrome for DNA like SYBR Gold and visualized under fluorescence microscopy.

Incubation with azithromycin, the antibiotic that inhibits the synthesis of proteins, did not result in modification of the bacteria which are similar in appearance to those from the cultures without antibiotics, in both susceptible and resistant strains to azithromycin.

Incubation with Triton-lysozyme-EDTA results in cell lysed showing nucleoids with fragmented DNA, as expected. The proportion of cells with DNA fragmentation can be variable in the different strains. In this case, the bacterial response comprises 84% and 93% DNA fragmentation in the susceptible and in the resistant strain, respectively.

Incubation with azithromycin followed by Triton-lysozyme-EDTA resulted in a strong decrease in the percentage of cells lysed and with fragmented DNA in the strain susceptible to azithromycin. In particular, the fragmented DNA was at about 40%, demonstrating 44% less fragmentation than incubation with Triton-lysozyme-EDTA alone. In contrast, the proportion of cells lysed and with fragmented DNA was 86% in the strain resistant to azithromycin, only 7% less.

Accordingly, it can be understood lysis and DNA fragmentation induced by Triton-lysozyme-EDTA is partially dependent on protein synthesis. If protein synthesis is successfully inhibited by azithromycin (i.e. in the strain susceptible to azithromycin), the frequency of cell lysed and showing DNA fragmentation induced by Triton-lysozyme-EDTA is strongly decreased. But, if the protein synthesis is not successfully inhibited by azithromycin (i.e. in the strain resistant to azithromycin), the proportion of cells lysed and with DNA fragmentation induced by Triton-lysozyme-EDTA remains unchanged or very less reduced. In this manner susceptible and non-susceptible strains can be rapidly discriminated with the assay. Similar responses were obtained using other antibiotic inhibitors of protein synthesis like the macrolide erythromycin and the tetracycline doxycycline.

Rapid Determination of Susceptibility or Non-Susceptibility to Antibiotics that Inhibit Protein Synthesis—Evaluating Responses at the Cell Wall Level.

Example 5

It has also been determined that the response of bacteria to the inhibitors of peptidoglycan synthesis; i.e. cell wall damage, is also influenced by ribosomal protein synthesis. The scaffold of the bacterial cell wall is composed of the peptidoglycan or murein. This is a linear chain constituted by alternant N-acetylglucosamine (NAG) and N-acetylmuramic acid (NAM). A tetrapeptide is attached to NAM, forming an interpeptidic bond with the tetrapeptide of the closest chain, stabilizing and strengthening the cell wall.

The main family of antibiotics that inhibit cell wall synthesis corresponds to the β-lactams. These are bactericidal agents that interfere with the formation of the interpeptidic bond through the inhibition of the Penicillin Binding Proteins (PBPs), serine proteases or transpeptidases, after an irreversible reaction. Secondarily, a build-up of peptidoglycan precursors triggers murein hydrolases or autolysins, degrading the peptidoglycan and resulting in cell death (Kitano K, Tomasz A. *Triggering of autolytic cell wall degradation in Escherichia coli by beta-lactam antibiotics. Antimicrob Agents Chemother* 1979, 16: 838-848).

The degradation of the peptidoglycan by agents that inhibit peptidoglycan synthesis is influenced by protein synthesis. Bacteria are first incubated with an antibiotic that affects protein synthesis followed by incubation with an antibiotic that inhibits peptidoglycan synthesis. If the bacteria are susceptible to the antibiotic that affects protein synthesis, the alteration of the peptidoglycan of the bacterial cell wall is reduced in comparison to that produced by incubation with the antibiotic that inhibits peptidoglycan synthesis alone. If, however, the bacteria are non-susceptible with respect to the antibiotic that affects protein synthesis, the level of affectation of the peptidoglycan by the antibiotic that inhibits peptidoglycan synthesis remains practically unchanged. In this case, the antibiotic that inhibits protein synthesis cannot act, so protein synthesis is effective and the peptidoglycan is degraded by the antibiotic that inhibits peptidoglycan synthesis. It may be apparent, this procedure may only be applied when the bacterial strain of interest is susceptible to the antibiotic that inhibits peptidoglycan synthesis.

As an exemplification of this principal, FIGS. 19-24 illustrates assays of two strains of *Pseudomonas aeruginosa* exponentially growing in Mueller-Hinton broth. Both strains were both susceptible to the β-lactam meropenem, which inhibits peptidoglycan synthesis. One strain was susceptible (FIGS. 19-21) and the other resistant (FIGS. 22-24) to the aminoglycoside tobramycin (inhibitor of protein synthesis).

For the purpose of rapidly distinguishing susceptible and resistant (i.e. non-susceptible) strains to tobramycin each strain was subjected to four treatments. A portion of each strain was incubated with tobramycin at 4 µg/ml for 75 min (FIGS. 19 and 22). The dose utilized, was indicated by the CLSI as the breakpoint of susceptibility to tobramycin. FIGS. 20 and 23 illustrate an assay from another portion of each strain, which was incubated with Meropenem at 0.2 µg/ml for 60 min. FIGS. 21 and 24, illustrate assays from still another portion of both strains which was incubated with tobramycin at 4 µg/ml for 15 min followed by meropenem at 0.2 µg/ml for 60 min, without removing the tobramycin. Still another portion of both strains was maintained without the addition of either antibiotic.

After incubation cells were processed using a variant Micromax technology to visualize the affectation or not of the cell wall based on the release or not of the nucleoids contained inside the bacteria. In the same manner described previously, samples from cells from the culture are immersed in an agarose microgel on a slide and incubated with a specific lysing solution that removes the cell wall only in those bacteria whose peptidoglycan was affected, thus releasing in the microgel the nucleoids contained inside. The bacteria whose cell wall is intact are not affected by the lysing solution and do not release the nucleoid, thus remaining with their standard shape. The processed bacteria in microgel are dried, stained with a high sensitive fluorochrome for DNA like SYBR Gold and visualized under fluorescence microscopy.

FIGS. 19 and 22 illustrate that incubation with tobramycin, the antibiotic that inhibits the synthesis of proteins, does not result in cell wall lysis and no modifications of the bacterial shape, which is similar in appearance to that from the cultures without antibiotics, in both susceptible and resistant strains to tobramycin.

FIGS. 20 and 23 illustrate incubation with meropenem results in releasing of nucleoids due to affectation of the cell wall. Moreover, a background of DNA fragments is evident. This result was observed in both strains since they are susceptible to meropenem.

FIG. 21 illustrates an assay of the susceptible strain incubated with tobramycin followed by meropenem resulting in unchanged, non-lysed bacteria. In contrast, the nucleoids were released and a background of DNA fragments was evident in FIG. 24 depicting an assay taken of the resistant culture under the same conditions. It can be seen FIG. 24 resembles FIGS. 20 and 23, the assays incubated with meropenem only.

Accordingly, peptidoglycan degradation by meropenem is dependent on protein synthesis. If protein synthesis is successfully inhibited by tobramycin (i.e. in the strain susceptible to tobramycin), the peptidoglycan affectation by meropenem is prevented. But if the protein synthesis is not successfully inhibited by tobramycin (i.e. in the strain resistant to tobramycin), the peptidoglycan affectation by meropenem remains unchanged. In this manner susceptible and non-susceptible strains can be rapidly discriminated with the assay.

Further exemplifying the concept described above twelve strains of *Klebsiella pneumoniae*, 7 susceptible and 5 resistant to tobramycin, were processed using the same rationale and procedure. Specifically, one portion of each was incubated with tobramycin at 4 µg/ml for 75 min. Another portion was incubated with Meropenem at 1 µg/ml for 60 min. Still another portion was incubated with tobramycin at 4 µg/ml for 15 minutes followed by meropenem at 1 µg/ml for 60 min, without removing the tobramycin. A final portion remained without any antibiotics.

In an evaluation of the assayed strains all the susceptible and the resistant (i.e. non-susceptible) strains to tobramycin were correctly identified with the rapid test. In the susceptible strains, successful inhibition of protein synthesis by tobramycin resulted in no appearance of cell wall lysis by meropenem when using the Micromax assay. Otherwise, in the tobramycin resistant strains, protein synthesis was not inhibited by the aminoglycoside, so the affectation of the cell wall by meropenem was not suppressed.

Example 6

Another cellular response affected by protein synthesis is cell lysis by peptidoglycan digestion which can be induced with cell wall lytic enzymes like lysozyme. When a bacteria like *Enterococcus*, gram positive, is incubated with lysozyme, it catalyzes the hydrolysis of beta 1,4-glycosidic linkages between N-acetylmuramic acid and N-acetylglucosamine of cell wall peptidoglycan. Later treatment with a lysing solution results in most of the cells being slightly lysed, thereby spreading the cytoplasm content, including fibers from the internal DNA-nucleoid. In certain embodiments of the present invention it has been demonstrated that when bacterial ribosomal protein synthesis is inhibited, the number of cells lysed by the lysozyme-lysing solution is greatly decreased. Nevertheless, when the bacterium is not susceptible to the dose of erythromycin or chloramphenicol, the percentage of lysed cells practically does not change with respect to the control culture only incubated with lysozyme but without the antibiotic.

As an example, two strains of *Enterococcus faecalis* exponentially growing in Mueller-Hinton broth were incubated under four different conditions and then assayed. One strain was susceptible to the macrolide erythromycin (inhibitor of protein synthesis) (MIC: 0.125 µg/ml) and the other resistant (MIC>128 µg/ml). Each strain was subjected to four treatments for the purpose of rapidly distinguishing the susceptible and the resistant strain to erythromycin.

A portion of each strain was incubated with erythromycin at 0.5 µg/ml for 75 minutes. The dose was that indicated by the CLSI as the breakpoint of susceptibility to erythromycin in the standard antibiogram based on microdilution. Another portion of both strains was incubated with lysozyme 1 mg/ml, 10 min at 37° C. Still another portion of both strains was incubated with Erythromycin at 0.5 µg/ml for 75 min followed by lysozyme 1 mg/ml during last 10 min, at 37° C.

After incubation with lysozyme, the cells were processed using a variant of the Micromax technology to visualize the nucleoids, i.e. spreading of the bacterial chromosomal DNA, in all the cells of the population. Samples from the cultures were immersed in an agarose microgel on a slide and incubated with a specific lysing solution to remove the cell wall in all the cells and release in the microgel the nucleoids contained inside the bacteria. These are dried, stained with a highly sensitive fluorochrome for DNA like SYBR Gold and visualized under fluorescence microscopy.

As can best be seen in FIG. 26, the assayed erythromycin-susceptible strain contained 92.13% lysed cells releasing nucleoid fibers after incubation with lysozyme and the lysing solution. As depicted in FIG. 27, the percentage of lysed cells dropped to 3.87% in the strain incubated with erythromycin prior to the introduction of lysozyme. As seen in FIG. 29, the assayed erythromycin-resistant strain, after incubation with lysozyme and lysing solution, contained 97.36% partially lysed cells with spreading nucleoid fibers. Prior incubation with erythromycin did not modify this percentage in the resistant strain. FIG. 30 depicts the assayed resistant strain having 96.77% lysed cells. To generalize these findings, a similar response pattern has been reproduced in four more erythromycin-susceptible and in thirteen more erythromycin-resistant *Enterococcus* strains. This inhibitory response has not been obtained after incubation with quinolones like ciprofloxacin, so the effect appears more specific of the inhibition of bacterial ribosomal protein synthesis.

Accordingly, cell lysis by cell wall lytic enzymes like lysozyme appears adversely affected by inhibition of protein synthesis in *Enterococcus*, and possibly in other species as well. If protein synthesis is successfully inhibited by erythromycin (i.e. in the strain susceptible to erythromycin), cell lysis by lysozyme and Micromax assay is decreased and most cells appear with their close standard shape. But if the protein synthesis is not successfully inhibited by erythromycin (i.e. in the strain resistant to erythromycin), cell lysis by lysozyme and Micromax assay is not suppressed or is much less suppressed and most of the bacteria remain lysed, thus releasing the nucleoids. In this manner susceptible and non-susceptible strains can be rapidly discriminated with the assay.

Rapid Determination of Susceptibility or Non-Susceptibility to Antibiotics that Inhibit Protein Synthesis—Evaluating Responses at the Morphological Level.

In further embodiments, it has been found that protein synthesis affects cell appearance modification, as cell enlargement induced by agents like antibiotics, DNA damaging or toxic agents.

Example 7

It has previously been demonstrated that bacteria susceptible to antibiotics that inhibit protein synthesis like the β-lactam, for example cephalosporines like ceftazidime, or carbapenems like meropenem, may induce cell enlargement in the susceptible strains at specific doses of the antibiotic. It has now been determined that this enlargement is dependent also on protein synthesis, so this effect can be suppressed in the bacterial strains susceptible to an antibiotic that inhibits protein synthesis whereas the effect remains in non-susceptible strains.

As an example, two strains of *Pseudomonas aeruginosa* exponentially growing in Mueller-Hinton broth were assayed. These strains were both susceptible to the β-lactam ceftazidime, which inhibits peptidoglycan synthesis. One strain was susceptible and the other resistant to the aminoglycoside tobramycin (an inhibitor of protein synthesis). For the purpose of rapidly distinguishing the susceptible and the resistant strain to tobramycin each strain was subjected to four treatments.

A portion of each strain was incubated with tobramycin at 4 µg/ml (the CLSI breakpoint of susceptibility) for 75 minutes. An assay of this portion is depicted at FIGS. 31 and 34. Another portion of each strain was incubated with ceftazidime at 0.5 µg/ml for 60 minutes. An assay of this portion is depicted at FIGS. 32 and 35. Still another portion of both strains was incubated with tobramycin at 4 µg/ml for 15 minutes followed by ceftazidime at 0.5 µg/ml for 60 minutes, without removing the tobramycin. Assays of these strains can be seen at FIGS. 33 and 36, respectively. A final portion of each strain was not treated with either antibiotic.

After incubation with the antibiotics, cells were processed using a variant Micromax technology to visualize the enlargement or not of the bacteria. Samples from each culture were immersed in an agarose microgel on a slide, dried, stained with a high sensitive fluorochrome for DNA like SYBR Gold and visualized under fluorescence microscopy to visualize cell shape and size.

FIGS. 31 and 34, illustrate that incubation with tobramycin, the antibiotic that inhibits the synthesis of proteins, does not affect the bacterial shape and size in either the susceptible or resistant strains. Both strains are similar in appearance to cultures without any antibiotics.

FIGS. 32 and 35, depict assays of bacteria incubated with ceftazidime resulting in significant cell enlargement. Similar results are seen in both strains since both are susceptible to ceftazidime.

FIG. 33 illustrates an assay of the susceptible bacteria incubated with tobramycin followed by ceftazidime resulting in bacteria with similar size to those incubated with tobramycin alone (FIG. 31) or untreated bacteria. In contrast, FIG. 36 depicts an assay of the resistant strain incubated under the same conditions in which bacteria appeared enlarged similarly to those from the culture incubated with ceftazidime only (FIG. 35).

Accordingly, enlargement by ceftazidime is dependent on protein synthesis and as such, the suppressing effects of protein synthesis inhibiting proteins can be employed for the rapid determination of susceptibility to protein synthesis inhibiting antibiotics. If protein synthesis is successfully inhibited by tobramycin (as it was in the strain susceptible to tobramycin), cell enlargement by meropenem is suppressed. But if the protein synthesis is not successfully inhibited by tobramycin (as it was in the strain resistant to tobramycin), cell enlargement by meropenem is not suppressed and the bacteria appear with higher length. In this manner susceptible and non-susceptible strains can be rapidly discriminated with the assay.

Example 8

It has further been discovered that relatively low doses of mitomycin C, an alkylating agent that induces DNA damage (see Example 3) can also affect the morphological appearance of bacteria. In particular, reduced dosages of mitomycin C may result in bacterial enlargement or alterations in size. It has further been discovered that this cell shape modification depends on protein synthesis. As such, this modification may be suppressed or reduced in the strains susceptible to the antibiotic that inhibits protein synthesis. In contrast, the cell shape modification remains in non-susceptible strains.

As an example, two strains of *Escherichia coli* exponentially growing in Mueller-Hinton broth were incubated under four different conditions and then assayed. One strain was susceptible and the other resistant to the aminoglycoside tobramycin (an inhibitor of protein synthesis). For the purpose of rapidly distinguishing susceptible and non-susceptible strains to tobramycin each strain was incubated under four conditions.

A portion of each strain was incubated with tobramycin at 4 µg/ml for 90 minutes. As described previously, this dose is indicated by the CLSI as the breakpoint of susceptibility to tobramycin in the standard antibiogram based on microdilution. Another portion of both strains was incubated in Mitomycin C at 0.5 µg/ml for 60 minutes. Still another portion of each strain was incubated with tobramycin at 4 µg/ml for 30 minutes followed by mitomycin C at 0.5 µg/ml for 60 minutes, without removing the tobramycin. A final portion of both strains was not incubated with either antibiotic.

After the incubation, cells were processed using a variant Micromax technology to visualize any enlargement or not of the bacteria. Samples from cells from the culture were immersed in an agarose microgel on a slide, dried, stained with a highly sensitive fluorochrome for DNA like SYBR Gold and visualized under fluorescence microscopy to visualize cell shape and size. Images were similar those correspondent to the previous figure.

The assayed bacteria revealed that incubation with tobramycin, the antibiotic that inhibits the synthesis of proteins, does not affect bacterial shape and size, which is similar in appearance to that from the cultures without antibiotics, in both susceptible and resistant strains to tobramycin.

Incubation with mitomycin C resulted in significant cell enlargement in both the susceptible and resistant strains of *E. coli*.

In the susceptible strain of bacteria, incubation with tobramycin followed by mitomycin C resulted in bacteria that were similar in size to those incubated with tobramycin alone or untreated bacteria. In contrast, the resistant bacteria incubated with tobramycin followed by mitomycin C appeared enlarged similarly to those from the culture incubated with mitomycin C alone.

Accordingly, it can be understood that cell enlargement induced by mitomycin C is dependent on protein synthesis. If protein synthesis is successfully inhibited by tobramycin, cell enlargement induced by mitomycin C is reduced or suppressed. But if the protein synthesis is not successfully inhibited by tobramycin, cell enlargement by mitomycin C is not suppressed and the bacteria appear with an enlarged length. This distinction provides a means for distinguishing susceptible and non-susceptible strains rapidly.

As demonstrated by Example 8, the evaluation of the suppression or not of cell enlargement by antibiotic inhibitors of protein synthesis can only be assessed in strains susceptible to the cell enlargement-inducing antibiotic. Nevertheless, the variant incorporating mitomycin C as the agent for inducing a bacterial response may have a more expanded application to many bacterial species and strains because no significant resistances to mitomycin C are expected.

This fact has been further exemplified, by using mitomycin C in the successful rapid detection of susceptibility-resistance to tobramycin in *Pseudomonas aeruginosa* and *Klebsiella pneumoniae*, as well as susceptibility-resistance to azithromycin in *Haemophilus influenzae*.

In one exemplification, two strains of *H. influenzae* exponentially growing in Mueller-Hinton broth were incubated under four differing treatments and then assayed. One strain was susceptible and the other resistant to the macrolide azithromycin (an inhibitor of protein synthesis). For the purpose of rapidly distinguishing the susceptible and the resistant strain to azithromycin each strain was incubated under four sets of conditions.

A portion of each strain was incubated with azithromycin at 4 µg/ml for 150 minutes. The dose azithromycin corresponded to the dose indicated by the CLSI as the breakpoint of susceptibility to azithromycin in the standard antibiograms based on microdilution. Another portion of each strain was incubated with Mitomycin C at 0.5 µg/ml for 120 minutes. Still another portion was incubated with azithromycin at 4 µg/ml for 30 min followed by mitomycin C at 0.5 µg/ml for 120 min, without removing the azithromycin. A final portion of each strain was not incubated with any antibiotics.

In the susceptible strain incubation with azithromycin followed by mitomycin C resulted in bacteria with similar size to those incubated with azithromycin or the untreated control. Otherwise, the bacteria appeared enlarged similarly to those from the culture incubated with mitomycin C only, in the strain resistant to azithromycin.

Other agents that induce DNA damage or cell toxicity resulting in cell shape modification could be used instead of antibiotics or mitomycin C. A non-exhaustive list or potential agents for inducing a bacterial response in the form of cell shape modifications includes alkylating agents, such as those often used in chemotherapy of cancer.

As can be easily understood from the foregoing, the basic concepts of the present invention may be embodied in a variety of ways. The invention involves numerous and varied embodiments including, but not limited to, the best mode of the invention.

As such, the particular embodiments or elements of the invention disclosed by the description or shown in the figures or tables accompanying this application are not intended to be limiting, but rather examples of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

Moreover, for the purposes of the present description and claims, the term "a" or "an" entity refers to one or more of that entity; for example, "an antibiotic" refers to one or more antibiotics. As such, the terms "a" or "an", "one or more" and "at least one" should be understood as interchangeable as used herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

In addition, as to each term used it should be understood that unless its utilization in this application is inconsistent with such interpretation, common dictionary definitions should be understood to be included in the description for each term as contained in the Random House Webster's Unabridged Dictionary, Second edition, each definition hereby incorporated by reference.

The background section of this patent application provides a statement of the field of endeavour to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of treating a patient comprising:
   incubating a first portion of a bacteria sample obtained from a patient with a breakpoint dosage of a protein synthesis inhibiting antibiotic;
   selecting an agent that will induce a bacterial response in the sample of bacteria that requires the same protein synthesis that is inhibited by the protein synthesis inhibiting antibiotic, wherein the bacterial response comprises changes in cell morphology in the form of changes in cell length, changes in cell size, changes in cell shape or combinations thereof;
   combining an effective amount of the agent selected to induce the bacterial response with the first portion of the bacteria during incubation with the breakpoint dosage of the protein synthesis inhibiting antibiotic;
   inducing, with the effective amount of the agent selected to induce the bacterial response, in a second portion of the bacteria sample that is not in the presence of the protein synthesis inhibiting antibiotic the same bacterial response that requires the same protein synthesis that is inhibited by the protein synthesis inhibiting antibiotic;
   classifying the bacteria sample as susceptible or non-susceptible to the protein synthesis inhibiting antibiotic based on a differences in cell morphology between bacteria in the first and second portions of the bacteria sample; and
   administering the protein synthesis inhibiting antibiotic to the patient upon the classification of the bacteria as susceptible to the protein synthesis inhibiting antibiotic.

2. The method as claimed in claim 1, wherein the steps of inducing the bacterial response that requires the same protein synthesis in the first and second portions of the bacteria sample further comprises the introduction of an agent selected from the following: DNA damaging agent, toxic agents, alkylating agents, mitomycin C, or combinations thereof.

3. The method as claimed in claim 1, wherein similarities in the bacterial response in the first and second portions of the bacteria sample are indicative of bacteria that is not susceptible to the protein synthesis inhibiting antibiotic.

4. The method as claimed in claim 1, wherein differences in the bacterial response in the first and second portions of the bacteria sample are indicative of bacteria that is susceptible to the protein synthesis inhibiting antibiotic.

5. The method as claimed in claim 1, wherein the extent of the bacterial response obtained in the first portion is decreased or supressed in comparison to the bacterial response obtained in the second portion, and decrease or suppression in the second portion is indicative of bacteria which is susceptible to the protein synthesis inhibiting antibiotic.

6. The method as claimed in claim 1, wherein the first portion of the bacteria sample is undergoing exponential growth at the time the bacterial response is induced.

7. The method as claimed in claim 1, wherein the second portion of the bacteria sample is undergoing exponential growth at the time the bacterial response is induced.

\* \* \* \* \*

UNITED STATES PATENT AND TRADEMARK OFFICE
CERTIFICATE OF CORRECTION

PATENT NO.       : 10,472,663 B2
APPLICATION NO.  : 15/000743
DATED            : November 12, 2019
INVENTOR(S)      : Jose Luis Fernández Garcia et al.

Page 1 of 1

It is certified that error appears in the above-identified patent and that said Letters Patent is hereby corrected as shown below:

In the Claims

Claim 1 Column 22 Line 61 replace "based on a differences in" with "based on differences in".

Signed and Sealed this
Seventeenth Day of March, 2020

Andrei Iancu
*Director of the United States Patent and Trademark Office*